United States Patent
Funk et al.

(10) Patent No.: US 9,186,524 B2
(45) Date of Patent: Nov. 17, 2015

(54) METHOD AND APPARATUS FOR LOCALIZED X-RAY RADIATION TREATMENT

(75) Inventors: Tobias Funk, Martinez, CA (US); Brian Patrick Wilfley, Los Altos, CA (US); Joseph Anthony Heanue, Oakland, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 435 days.

(21) Appl. No.: 13/538,212

(22) Filed: Jun. 29, 2012

(65) Prior Publication Data

US 2013/0003931 A1    Jan. 3, 2013

Related U.S. Application Data

(60) Provisional application No. 61/502,775, filed on Jun. 29, 2011.

(51) Int. Cl.
*A61N 5/10* (2006.01)
*H01J 35/32* (2006.01)

(52) U.S. Cl.
CPC ............. *A61N 5/1014* (2013.01); *A61N 5/1001* (2013.01); *A61N 5/1015* (2013.01); *A61N 2005/1022* (2013.01); *H01J 35/32* (2013.01)

(58) Field of Classification Search
CPC ..... A61N 5/10; A61N 5/1001; A61N 5/1007; A61N 5/1014; A61N 5/1022; A61N 5/1028; A61N 2005/1003; A61N 2005/1005; A61N 2005/1095; H01J 35/16; H01J 35/18; H01J 35/20; G21K 5/00; G21K 5/02; G21K 1/062
See application file for complete search history.

(56) References Cited

U.S. PATENT DOCUMENTS

| | | | |
|---|---|---|---|
| 4,274,005 A | 6/1981 | Yamamura et al. | |
| 5,442,678 A | * 8/1995 | Dinsmore et al. | ............ 378/137 |
| 5,651,047 A | 7/1997 | Moorman et al. | |
| 5,682,412 A | 10/1997 | Skillicorn et al. | |
| 5,808,306 A | 9/1998 | Skillicorn et al. | |
| 6,118,853 A | 9/2000 | Hansen et al. | |
| 6,118,854 A | 9/2000 | Solomon et al. | |

(Continued)

FOREIGN PATENT DOCUMENTS

KR    20100134981    * 12/2010    ............... H05G 1/02

OTHER PUBLICATIONS

Basavaraj et al., Local Liquid Holdups and Hysteresis in a 2-D Packed Bed Using X-ray Radiography, Aug. 2005,Particle Technology and Fluidization, AIChE Journal, vol. 51, No. 8, p. 2179-2181.*

(Continued)

*Primary Examiner* — Irakli Kiknadze
*Assistant Examiner* — Julio M Duarte-Carvajalino
(74) *Attorney, Agent, or Firm* — Sabrina N. David; Joseph T. Lin (57) ABSTRACT

The present invention pertains to a system for electronic brachytherapy wherein a layer of target material can produce reflection and transmission X-rays when struck by electrons from a cathode. An alternative system can have a fixed-size containment structure around a miniature X-ray source, with X-ray attenuating coolant fluid between the source and containment structure. A balloon can be around the fixed-size containment structure and can be inflated with an X-ray inert gas.

20 Claims, 5 Drawing Sheets

(56) References Cited

U.S. PATENT DOCUMENTS

| | | | |
|---|---|---|---|
| 6,148,061 A * | 11/2000 | Shefer et al. | 378/121 |
| 6,157,703 A | 12/2000 | Solomon et al. | |
| 6,175,611 B1 | 1/2001 | Melen et al. | |
| 6,178,223 B1 | 1/2001 | Solomon et al. | |
| 6,181,764 B1 | 1/2001 | Solomon et al. | |
| 6,198,802 B1 | 3/2001 | Elliott et al. | |
| 6,208,709 B1 | 3/2001 | Melen | |
| 6,234,671 B1 | 5/2001 | Solomon et al. | |
| 6,421,416 B1 * | 7/2002 | Sliski et al. | 378/65 |
| 7,023,950 B1 | 4/2006 | Annis | |
| 7,062,006 B1 | 6/2006 | Pelc et al. | |
| 8,050,384 B2 | 11/2011 | Carol et al. | |
| 8,520,800 B2 | 8/2013 | Wilfley et al. | |
| 2002/0003856 A1 * | 1/2002 | Gutman | 378/65 |
| 2004/0017889 A1 | 1/2004 | Kumakhov | |
| 2005/0063510 A1 | 3/2005 | Hieronimi et al. | |
| 2006/0126788 A1 * | 6/2006 | Engel | 378/119 |
| 2009/0084933 A1 | 4/2009 | Appleby et al. | |
| 2009/0274269 A1 | 11/2009 | Foland et al. | |
| 2011/0058647 A1 | 3/2011 | Star-Lack et al. | |

OTHER PUBLICATIONS

Gaines, J. L., et al. "Facilities and techniques for x-ray diagnostic calibration in the 100-eV to 100keV energy range." Proceedings of SPIE, 30th Annual Technical Symposium on Optical and Optoelectronic Applied Sciences and Engineering, Aug. 1986. USA.

* cited by examiner

METHOD AND APPARATUS FOR LOCALIZED X-RAY RADIATION TREATMENT

CROSS-REFERENCE TO RELATED U.S. APPLICATIONS

This application claims priority to the co-pending U.S. provisional patent application, Ser. No. 61/502,775, entitled "Method and Apparatus for Localized X-ray Radiation Treatment," with filing date Jun. 29, 2011, which is hereby incorporated by reference in its entirety.

FIELD OF THE INVENTION

The present invention is in the field of radiation treatment. The present invention is also in the field of electronic brachytherapy.

BACKGROUND

Radiation treatment can involve the deposition of high-energy radiation in human tissue for the purpose of destroying malignant or unhealthy tissue. This treatment may be performed with an external radiation source. As a side effect, other tissue between or around the source and targeted treatment area may be irradiated and possibly damaged during this type of treatment.

Radiation treatment can also be performed intraoperatively or post-operatively; for example, brachytherapy can be performed following the surgical removal of a cancerous tissue. Conventional brachytherapy involves the placement of a radioactive material on or near the tissue intended for treatment. In some cases, this can include the insertion of the radioactive material, or radioactive seed, into a surgical cavity, for example following a mastectomy or lumpectomy. The radioactive seed or seeds can be left inside a patient for minutes up to days, or in some cases permanently.

Conventional brachytherapy can be cumbersome in an operating-room environment. For example, due to handling procedures of radioactive material involved, staff may need to leave the room during the treatment and the material delivered through an operator-controlled afterloading machine. Furthermore, it can be difficult to optimize treatment plans using radioactive seeds.

Electronic brachytherapy is an emergent field utilizing miniature X-ray sources for localized radiation treatment. While electronic brachytherapy can provide an alternative to radioactive handling, uniformly irradiating a treatment margin with existing miniature X-ray sources can require relatively complex treatment planning. Conversely, implementing non-uniform radiation patterns which selectively underdose healthy or sensitive tissue can also be difficult with existing brachytherapy systems. What is needed is an advanced electronic brachytherapy system which can implement a predetermined uniform or non-uniform radiation pattern.

SUMMARY

The present invention pertains to a system for electronic brachytherapy wherein a layer of target material can produce reflection and transmission X-rays when struck by electrons from a cathode. The layer of target material may be a metal with an atomic number greater than 40 and have a thickness between 1 µm and 150 µm. The layer can be configured to absorb at least 70% of the electrons that strike it. This layer may also be deposited on a substrate material, which can either be positioned within the vacuum chamber or form the vacuum chamber, such as by being a spherical or ellipsoidal shell within which the target material is deposited. The substrate material may be between 0.1mm and 5mm thick.

An alternative system can have a fixed-size containment structure around a miniature X-ray source, with X-ray attenuating coolant fluid between the source and containment structure. A balloon can be around the fixed-size containment structure and can be inflated with an X-ray inert gas. The X-ray attenuating coolant fluid can be an ionic solution, the ions of which may have an atomic number greater than 11, such as iodine. The gap between the fixed-size containment structure and the miniature X-ray source, which may be between 1 mm and 7 mm wide. The X-ray inert gas can be air, or can include nitrogen or helium. The miniature X-ray source, coolant fluid, and fixed-size containment can produce an X-ray radiation pattern of uniform hardness.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

A method and apparatus is described for radiation treatment in oncology, vascular disease including peripheral and coronary artery disease, nerve ablation, and similar conditions. One embodiment of the present invention can be used for radiation treatment of tumor beds after surgery. In some embodiments a miniature X-ray source, which may have an X-ray spectrum between 1 keV and 100 keV and be designed to deliver a spherical radiation pattern for fast treatment during surgery or radiation treatment, can be utilized. In other embodiments a non-uniform radiation pattern can be tailored to treat diseased tissue and spare healthy tissue. In one embodiment, a non-uniform radiation pattern may be tailored by selectively attenuating the X-ray source with metal shields. In another embodiment, X-ray sources with different, non-uniform radiation patterns can be positioned to one or multiple locations within the balloon.

Embodiments of the present invention may deliver 2 Gy to 30 Gy in 2 min to 120 min or 25 min in the treatment margin of 3 mm to 2 cm or 1 cm. Alternatively, embodiments may deliver an absorbed dose between 1 Gy and 1.5 Gy, 1.5 Gy and 2 Gy, 2 Gy and 2.5 Gy, 2.5 Gy and 3 Gy, 3 Gy and 3.5 Gy, or 3.5 Gy and 4 Gy, inclusive, or any other integer or non-integer amount of dose within the enumerated ranges. For example, an embodiment of the present invention may deliver 1.8 Gy, 1.9 Gy, 2 Gy, 2.1 Gy, or 2.2 Gy. Other embodiments may deliver an absorbed dose between 2 Gy and 6 Gy, 6 Gy and 10 Gy, 10 Gy and 14 Gy, 14 Gy and 18 Gy, 18 Gy and 22 Gy, 22 Gy and 26 Gy, or 26 Gy and 30 Gy, inclusive, or any integer or non-integer amount of dose within the enumerated ranges.

An absorbed dose can be delivered over a single exposure time or through serial exposures. For example, a 10 Gy dose may be delivered through a series of ten treatments each delivering 1 Gy, five treatments each delivering 2 Gy, or other combinations. As an additional example, a 30 Gy dose may be delivered through a series of fifteen treatments each delivering 2 Gy, twenty treatments each delivering 1.5 Gy, thirty treatments each delivering 1 Gy, and so forth.

Embodiments may deliver dose over exposure times including any length of time between 2 min and 120 min, 2 min and 60 min, 2 min and 25 min, inclusive, and any number of minutes or seconds within the enumerated ranges. For example, embodiments of the present invention may locally irradiate tissue for between 2 min and 5 min, 5 min and 10 min, 10 min and 30 min, 30 min and 60 min, or 60 min and 120 min, inclusive. Alternatively, an embodiment may deliver dose over an exposure time less than 2 min, such as between 30 sec and 60 sec, 60 sec and 90 sec, or 90 sec and 120 sec, inclusive.

Tissue may be irradiated to any depth between 3 mm and 2 cm, 3 mm and 1 cm, 3 mm and 0.5 cm, inclusive, and any integer or non-integer depth within the enumerated ranges by embodiments of the present invention.

Dose drop-off can describe the rate and manner in which X-ray dose is distributed in tissue. Dose drop-off can be related to the absorption and scattering properties of the tissue and the energy spectrum or hardness of incident X-rays. In embodiments of the present invention, X-ray spectra in the range of 1 keV to 100 keV, 20 keV to 80 keV, or 30 keV to 60 keV can be used. Expected dose-drop off in any direction from a source in embodiments of the present invention can be simulated or predicted through simulation, given the geometry of the configuration, X-ray spectrum, and other parameters. TG-43 dosimetry parameters from the American Association of Physicists in Medicine, which have been calculated for some electronic brachytherapy sources, can be utilized for these simulations.

In embodiments of the present invention, X-ray spectra can be designed to have a fast dose drop-off beyond the treatment margin intended for irradiation. In one embodiment, a dose drop-off of 10% to 80% of the treatment dose at 2 mm to 1 cm beyond the treatment margin can be achieved. This dose drop-off can result in malignant cells or tissues in the treatment margin being treated with a high dose of radiation with healthy cells and tissues outside the treatment margin receiving very little to no dose.

In one embodiment of the present invention, a radiation source can be housed in an inflatable balloon. The balloon can be inserted in a cavity created by removal of a tumor or cancerous tissue, or any other surgical cavity. The balloon can have a spherical or ellipsoidal shape. Its diameter or length when inflated may be in the range of 0.5 cm to 15 cm. Its inflated diameter or length may further be in the range of 0.5 cm to 1 cm, 1 cm to 3 cm, 3 cm to 5 cm, 5 cm to 7 cm, or 7 cm to 10 cm, inclusive, and any integer or non-integer number of centimeters within the enumerated ranges. It can be inflated with a gas, including but not limited to air, nitrogen, helium, or argon, or with liquids, including but not limited to water or saline solution.

In another embodiment of the invention, the source can be surrounded by a fixed-sized containment structure. The fixed-size containment structure may be a balloon, a spherical shell, or a shell of any other shape. The diameter or length of the fixed-size containment structure may range from 0.3 cm to 3 cm. For example, the fixed-size containment structure may have a diameter or length between 0.3 cm and 0.6 cm, 0.6 cm and 0.9 cm, 0.9 cm and 1.2 cm, 1.2 cm and 1.5 cm, 1.5 cm and 1.8 cm, 1.8 cm and 2.1 cm and 2.4 cm, 2.4 cm and 2.7 cm, or 2.7 cm and 3.0 cm, inclusive, or any other integer or non-integer number of centimeters within the enumerated ranges.

A fixed-size containment structure may be a balloon fabricated from a material that becomes non-compliant upon a predetermined amount of inflation, e.g. pressure. Such materials may include but are not limited to polyvinal chloride (PVC), crosslinked polyethylene (PE) or other polyolefins, polyethylene terephthalate (PET), nylons, polyurethanes, and other polymers. A balloon fabricated from one or more of these materials with sufficient wall thickness may maintain predetermined dimensions for a range of pressures between a minimum pressure and a burst pressure, in contrast to a balloon fabricated from a more compliant material or with thinner walls, the dimensions of which may continue to expand with increasing pressure up to a burst pressure.

Sufficient wall thickness for a balloon to become non-compliant may be highly material-dependent and may be in the range of 5 µm to 1 mm. Wall thickness can also be varied for attenuation purposes, as previously described.

A fixed-size containment structure may also be a shell made from metals, e.g. aluminum or copper, or polymers, e.g. plastic, rubber, silicone, or another natural or synthetic polymer.

Containment structures in embodiments of the present invention may increase the efficacy of radiation treatment. In one embodiment of the present invention, a fixed-size, e.g. non-compliant, balloon can define the treatment volume in a surgical cavity. It can slightly stretch surrounding tissue such that flaps or crevices are spread out and a large area of tissue comes in contact with the walls of the balloon. In this manner, the balloon can establish a cavity geometry that matches the geometry utilized for pre-procedural treatment planning. Furthermore, alleviation of irregularities such as tissue folds or crevices can better expose the treatment margin to radiation from the source.

A balloon of an optimal size and shape can be selected prior to surgery, such as through a diagnostic CT scan; during surgery, such as through direct observation; or after surgery, such as through a CT scan or other imaging method. A fixed-size, spherical or ellipsoidal balloon may be selected that best fits the size and shape parameters of the cavity. Alternatively, a flexible, e.g. compliant or semi-compliant, balloon may be selected and may conform to a cavity. In an embodiment wherein a flexible balloon conforms to a cavity, a diagnostic CT scan may be utilized to predict the shape to which the balloon will conform, and a treatment plan can be tailored to this geometry.

The fixed-size containment structure may contain coolant fluid, which can flow around the radiation source and prevent overheating of the source. It may also be configured to affect the radiation pattern received by surrounding tissue, for example by variations in thickness or other shape characteristics.

In a further embodiment of the present invention, a balloon can surround the fixed-sized containment structure. In this embodiment, the balloon can be inflatable up to a size or range of sizes between 10 ml and 300 ml so it can conform to or establish the geometry of the treatment margin. This outer balloon can be inflated with gas, including but not limited to nitrogen, air, helium, argon, or any combination thereof, and thereby preserve the beam hardness emitted by the containment structure.

Beam hardness can describe the distribution of energies of the photons in an X-ray beam. An X-ray beam with an energy distribution having a high mean energy is harder than a beam with an energy distribution having a low mean energy. A soft or unfiltered beam may deposit a large fraction of its energy in a shallow depth of tissue since photon energy can correspond to the stopping time for that photon in tissue; a low-energy photon can be stopped more quickly, e.g. in a shallower depth of tissue, than a high-energy photon. A harder beam may deposit energy throughout a deeper volume of tissue. Thus, having a predetermined beam hardness can be important for accurate calculation of the absorbed dose and dose drop-off that can occur in tissue.

When a beam passes through an attenuating material or filter, some range of photon energies may be more highly attenuated than others, narrowing the energy distribution of the beam to those energies which were less attenuated. In some embodiments of the present invention, a containment structure or containment structures can affect beam hardness in a predetermined manner. For example, a fixed-size containment structure can be fabricated from aluminum, copper, or another metal. The atomic structure of metals, such as aluminum and copper, may result in highly selective attenuation of low-energy X-ray photons, e.g. in a range between 1 keV to 10 keV. This selective attenuation of photons via photoelectric interaction may harden an incident X-ray beam or X-ray spectrum. Alternatively, a fixed-size containment structure can be fabricated from a polymer or plastic. A polymer or plastic containment structure may attenuate X-ray photons of different energies more evenly. It may therefore affect the overall intensity of an X-ray beam without significantly affecting the beam's hardness.

In embodiments of the present invention, a containment structure can be filled with a gas or other substance which does not interact significantly with X-rays. Such embodiments utilizing an X-ray inert medium to inflate or fill a containment structure may preserve the hardness of an X-ray beam during transit from the anode to the walls of the structure.

Alternatively, a containment structure can be filled with a fluid such as water or a solution which can absorb or otherwise attenuate X-rays. A fluid may further be deionized water, saline solution, or another ionic solution. An ionic solution in which ions with an atomic number greater than 11 may be utilized to significantly affect beam hardness. For example, an ionic solution containing potassium or iodine ions may attenuate X-rays more strongly than an ionic solution containing sodium and therefore harden an X-ray beam to a greater extent.

Figure 7:
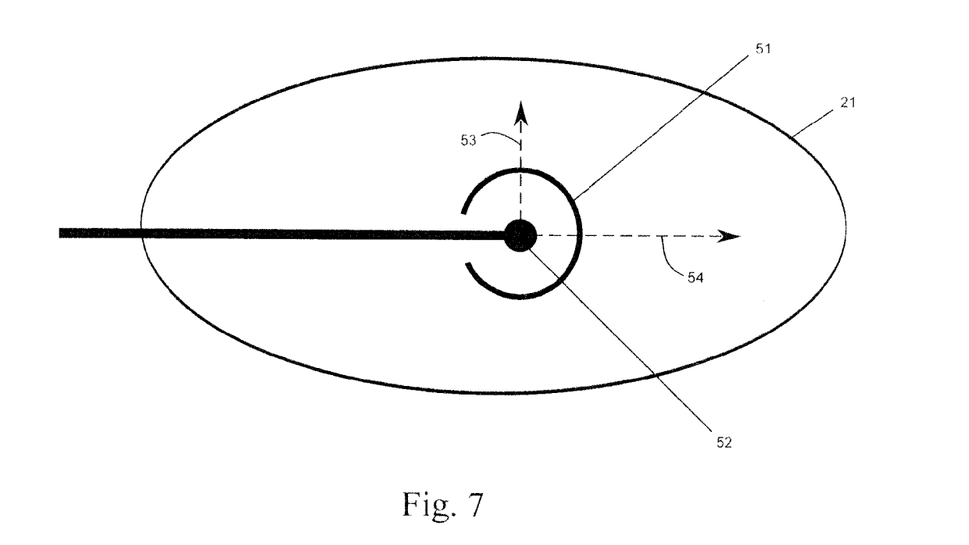
FIG. 7 is a diagram showing an embodiment of the present invention, wherein the anode is a spherical transmission target with only a small opening for insertion of the cathode.

In these embodiments, the distance from the anode to a wall of the containment structure in a given direction can affect the intensity or hardness of an X-ray beam in that direction; as the beam may be attenuated along its path by the water or solution, a longer path through solution may result in greater attenuation or filtration. For example, if containment structure 21 as shown in the embodiment of FIG. 7 were filled with an attenuating liquid then an X-ray beam may be more highly attenuated in direction 54 than in direction 53 such that the radiation pattern outside of containment structure 21 may be more intense in direction 53 than in direction 54.

In one embodiment of the present invention, a fixed-size containment structure can be placed within a cavity during surgery or surgically implanted. This may allow the fixed-size containment structure to be larger than if it had to be inserted through an open orifice to the cavity for each post-operative treatment. An outer, inflatable containment structure can also be placed within the cavity during surgery such that post-operative radiation treatment can require insertion and removal of only an X-ray source through an orifice into the cavity.

In some embodiments of the present invention, the inner containment structure can have a non-symmetrical shape. In these embodiments, the inner containment structure can be designed to tailor the radiation pattern emitted from the X-ray source, such as by varying the thickness or material composition of the containment structure. For example, sections of the structure may be thickened or fabricated from a more highly attenuating material relative to other section in order to decrease radiation in some regions of the radiation pattern. Within the containment structure a cooling liquid can be circulated to cool the X-ray tube. The containment structure can be made from plastics, metal such as aluminum, or similar.

Figure 1:
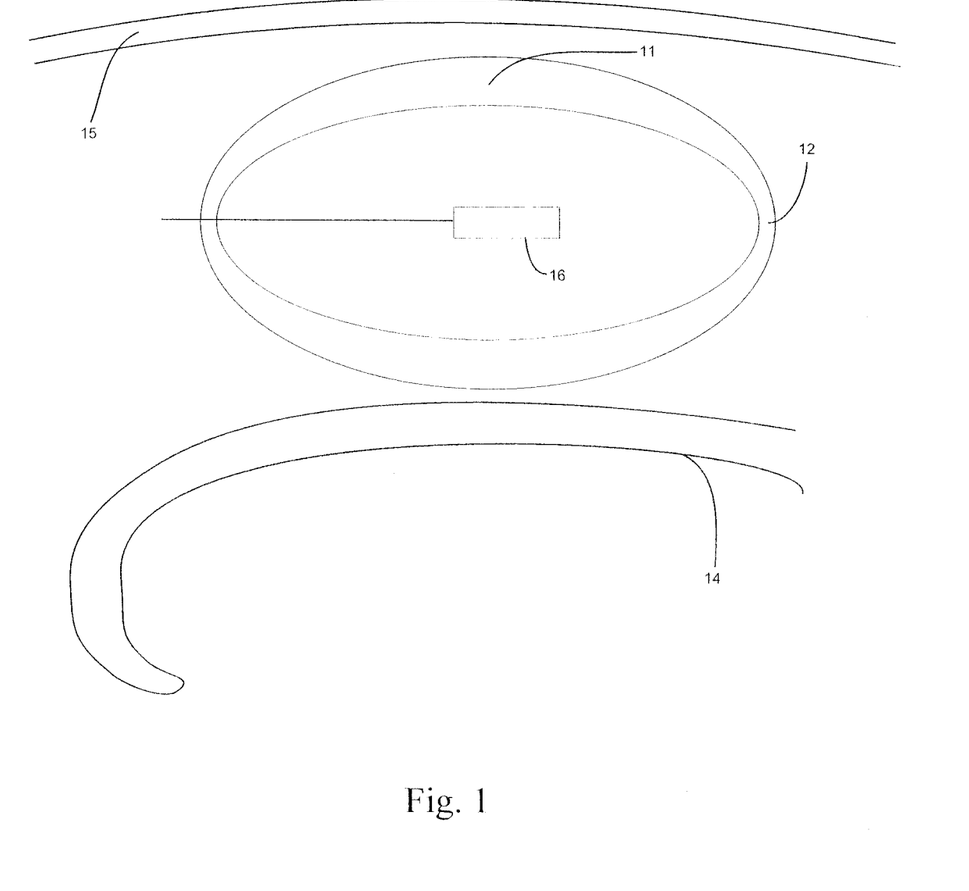
FIG. 1 is a diagram showing one embodiment of the present invention utilizing an ellipsoidal outer containment structure tailored to attenuate radiation asymmetrically.

FIG. 1 is a diagram showing one embodiment of the present invention utilizing an ellipsoidal outer containment structure tailored to attenuate radiation non-symmetrically. In FIG. 1, thickened region 11 can attenuate more X-ray radiation than thin region 12, such that tissue near thickened region 11 may be irradiated relatively less than tissue near thin region 12. This embodiment may be particularly useful for cavities located adjacent to or between radiation-sensitive, healthy tissue such as bone or skin. For example, the embodiment of FIG. 1 may be located between rib 14 and skin 15. A radiation pattern created by this embodiment can be relatively intense in possibly malignant tissue regions adjacent thin region 12 and less intense in rib 14 and skin 15.

In this embodiment, source 16 can emit X-rays in an isotropic or symmetric pattern or may emit X-rays in a directional or non-symmetric pattern. Source 16 can emit X-rays from a fixed position or be moved or rotated during the procedure, as discussed below. Inside the containment structure may be a liquid or gas, as previously described, which can preserve or increase beam hardness in a predetermined manner. An inner containment structure may or may not be included in this embodiment.

The embodiment of FIG. 1 may also be utilized for uniform irradiation of a treatment margin. For example, source 16 may provide a spherically uniform radiation pattern. However, in an ellipsoidal cavity such as that shown in FIG. 1, a lower density of X-rays may reach thin region 12 than thickened region 11 since the distance to thin region 12 is greater. X-ray intensity can decrease exponentially with distance from a source, e.g. proportionally to $1/r^2$ with r being distance from a source. The thickness of thickened region 11 can be tailored to attenuate a sufficient number of X-rays such that the X-ray intensity entering a treatment margin at thickened region 11 equals the X-ray intensity entering a treatment margin at thin region 12. The thickness variation along the walls of a containment structure, e.g. between the thickest part of region 11 and thinnest part of region 12, can similarly be tailored to distances from source 16 to uniformly irradiate an ellipsoidal treatment margin.

In an alternative embodiment of the present invention, an inner containment structure may have thickness variations such as those shown in FIG. 1. In this embodiment, an outer containment structure may further tailor the radiation pattern or may attenuate radiation uniformly.

This and other embodiments which can create a uniform, e.g. spherically uniform, radiation pattern may be particularly useful for surgical and post-surgical use. Treatment plans for a procedure utilizing a non-uniform radiation pattern may involve rotating, sliding, or otherwise manipulating the source between or during dose deliveries in order to irradiate all sections of a treatment margin. A treatment plan for a source with a uniform radiation pattern may comprise as little as positioning the source in the center of a cavity, e.g. center of a containment structure or balloon, and irradiating the cavity for a predetermined amount of time at a given energy from this single position.

In X-ray sources, a voltage difference between an electron emitter and a target surface can accelerate electrons so that they hit the surface with energy sufficient to cause X-ray emission from the target material. In embodiments of the present invention, this voltage difference can be created by holding the electron emitter at one voltage, and holding the target surface at a different, less-negative or more-positive voltage. The electrons may also or alternatively be accelerated by separate electrodes along the electron path. However, in this description cathode may refer to an electron emitter and anode to an X-ray emissive target surface, irrespective of the presence of additional electrodes or specific voltages of elements of the X-ray source.

Figure 2:
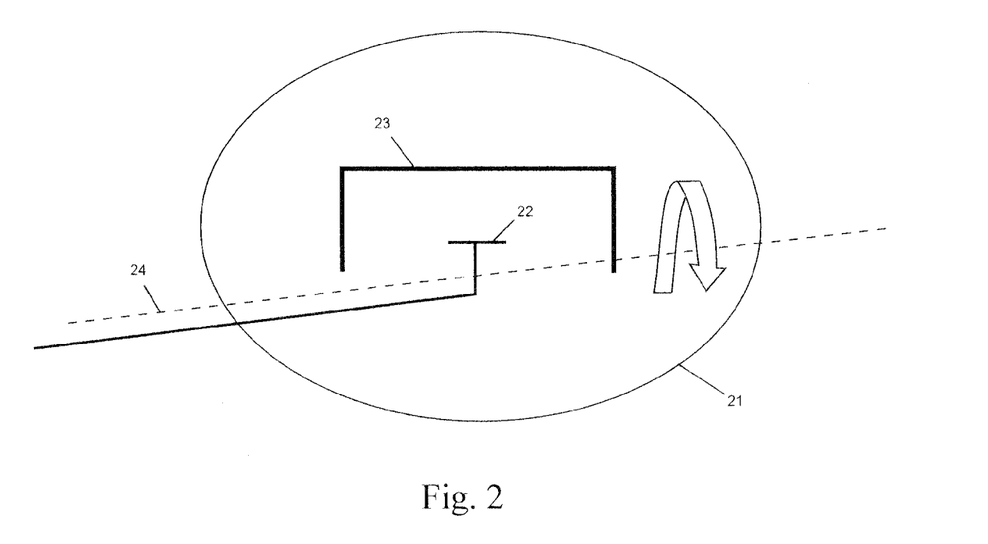
FIG. 2 is a diagram showing an embodiment of the present invention wherein the anode is shaped like a half cuboid.
Figure 3:
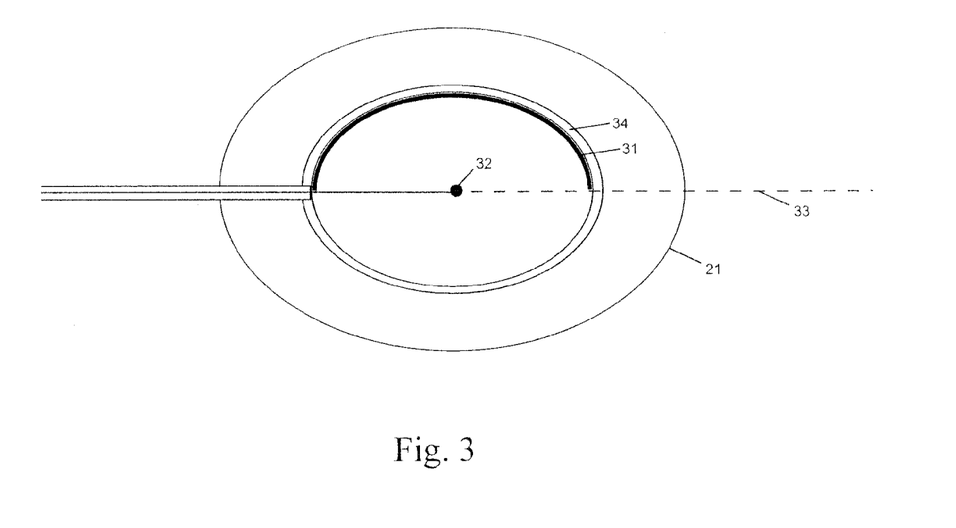
FIG. 3 is a diagram showing an embodiment of the present invention wherein the anode is shaped like a half ellipsoid.

In one embodiment of the present invention, the X-ray source can have an anode that is shaped like a half cuboid or half ellipsoid with the cathode positioned close the center of the geometrical shape. FIG. 2 is a diagram showing an embodiment of the present invention wherein the anode is shaped like a half cuboid. FIG. 3 is a diagram showing an embodiment of the present invention wherein the anode is shaped like a half ellipsoid. FIG. 2 and FIG. 3 represent cross-sectional views of a containment structure surrounding an anode and cathode. In these figures, containment structure 21 is ellipsoidal, but it may also be spherical or any other shape. An additional inner or outer containment structure may also be included. Vacuum can be maintained between the cathode and anode by a containment structure, separate vacuum chamber, or other means.

The X-ray sources of the embodiments of FIG. 2 and FIG. 3 and similar embodiments may deliver radiation to a treatment margin in a manner that is more selective or directional than a forward-emitting or symmetric source. For example, anode 23 or anode 31 may be a transmission target such that, in the configuration of FIG. 2 or FIG. 3, radiation would only be delivered to the upper hemisphere of containment structure 21 or some subset thereof. Thus, if containment structure 21 were positioned near radiation-sensitive tissue or bone, e.g. skin 14 or rib 15, radiation from anode 23 or anode 31 may be directed towards target regions in the treatment margin and away from these radiation-sensitive or healthy areas.

Anode 23, anode 31, or similar anodes may be configured to irradiate a predetermined solid angle of the surgical cavity. For example, anode 31 may irradiate $2\pi$ steradians (sr), e.g. exactly half of the surgical cavity. Alternatively, anode 31 may illuminate less than $2\pi$ sr, such as between 0 and $2\pi/3$ sr, $2\pi/3$ sr and $4\pi/3$ sr, or $4\pi/3$ sr and $2\pi$ sr, inclusive. Irradiation of smaller solid angles can result in the source enabling a greater amount of directional selectivity during treatment of tissue surrounding a surgical cavity. The solid angle irradiated by the source can be determined by the shape of the anode or by deflection or focusing of electrons from the cathode. Deflection or focusing may be accomplished with additional electrodes or other means. As discussed below, the anode, cathode, or both, may be rotated during a procedure such that a uniform or non-uniform radiation pattern may be created by a directional source.

In other embodiments of the present invention, the X-ray source can be shaped like a partial cuboid, ellipsoid, or any other shape. The shape may be symmetric or asymmetric, and may be centered within a containment structure or off-center.

The X-ray source can be rotated about an axis of rotation during treatment. The rate of rotation may be at least one revolution during the duration of the procedure, but can also be as high as 10 revolutions per minute. Alternatively, the X-ray source can complete less than one 360-degree revolution during the duration of the procedure. For example, if the X-ray source is designed to irradiate half of a cavity, e.g. $2\pi$ sr, then the entire cavity may be illuminated in 0.5 revolutions, e.g. a 180-degree rotation.

In one embodiment of the invention the axis of rotation can coincide with the symmetry axis of a balloon or containment structure. For example, in FIG. 3, anode 31, cathode 32, and containment structure 21 may be rotated around major axis 33 of containment structure 21. In another embodiment the rotation axis can have an asymmetric location and may allow for more uniform irradiation in the forward and backward direction. For example, in FIG. 2 anode 23 is oriented such that asymmetric axis of rotation 24 can be utilized.

In a fixed position, an X-ray source can have a non-spherical radiation pattern in the azimuthal direction, e.g. around an axis of rotation. Rotation of the source may create a uniform radiation pattern. Alternatively, the rotation speed can be varied and an intentionally non-uniform radiation pattern thereby created. A non-uniform radiation pattern can also be created by modulating the intensity of the source during rotation. This can be useful to spare radiation sensitive organs such as bone or skin.

In a further embodiment of the present invention, an X-ray source can be moved linearly, with or without rotation. For example, in the configuration of FIG. 3, a source may irradiate tissue at one location along major axis 33 of containment structure 21. It may or may not be rotated during irradiation. The source may then be slid along major axis 33 to a second position, and may irradiate tissue at the second position. This process may be repeated over any number of increments. The source may be slid over small length increments, such as 1 mm, 1.5 mm, 2 mm, 2.5 mm, 3 mm, 3.5 mm, 4 mm, 4.5 mm, or any integer of non-integer number of millimeters between the enumerated values. Alternatively, the source may be slid over larger length increments, such as between 0.5 cm and 1 cm, 1.5 cm and 2 cm, and so forth.

In another embodiment of the present invention, the source may be continuously slid along an axis during radiation treatment. The source can also be rotated, e.g. such that the anode follows a helical path. The source may emit a constant amount of radiation during the movement of the source, or may be turned on and off or otherwise modulated.

In some embodiments of the present invention, a radiation pattern can be designed to an intended uniformity or non-uniformity by shaping the anode. Electrons or an electron beam which irradiate the anode can be generated by a cathode that is either inside or outside a containment structure. If the cathode is outside the shell, an electron beam may travel inside an evacuated tube to the anode. While such a configuration may require precise alignment among the evacuated tube, cathode, and anode and possibly the introduction of additional focusing elements or electrodes, it may also allow a relatively larger cathode or emitter to be used. Non-miniature X-ray source components may utilize higher peak voltages, be less difficult to manufacture, or have other performance advantages.

The anode can act as a reflection target, a transmission target, or both a transmission target and a reflection target at the same time. In the case that the anode acts as both a transmission target and a reflection target, the anode may be a thin-layer target between 1 µm and 150 µm made from tungsten, molybdenum, rhenium, gold, niobium or any combination of those or other metals on a substrate made from beryllium, ceramics, or similar materials. Possible substrate properties are detailed below. Target materials may include additional metals with an atomic number greater than 40. The thickness of a layer of target material in the anode may also be in the range of 1 µm to 100 µm, 1 µm to 50 µm, or 5 µm to 20 µm, inclusive. This layer thickness can be designed to allow transmission in the forward direction and reflection in the backward direction.

In one embodiment of the present invention, a method for determining a target material layer thickness that may allow the anode to act as both a transmission target and a reflection target may be to calculate the penetration depth of electrons in the target material. The thickness of the material being greater than the penetration depth of all electrons may result in very few transmission X-rays, inhibiting the anode from acting as a transmission target. However, the thickness of material being less than the penetration depth of most electrons can allow most electrons to pass through the anode without generating X-ray emission.

Electron penetration depth can be predicted analytically, via simulation such as Monte Carlo simulation, or in any other manner for a given X-ray energy or energy spectrum and a given anode target material. Simulations may utilize the Monte Carlo package EGSnrc or any other inputs or models for the probabilities of interactions between electrons of a given energy and a material. For example, an incident electron beam can be simulated and its electrons traced through the material. Energy deposited in the material at various depths by each interaction event between an electron and the material may be calculated. A histogram or curve, e.g. depth in the material verse intensity, where energy or intensity can indicate the presence of electrons can be generated. This curve or histogram can be the penetration depth profile for the electron beam.

Figure 4:
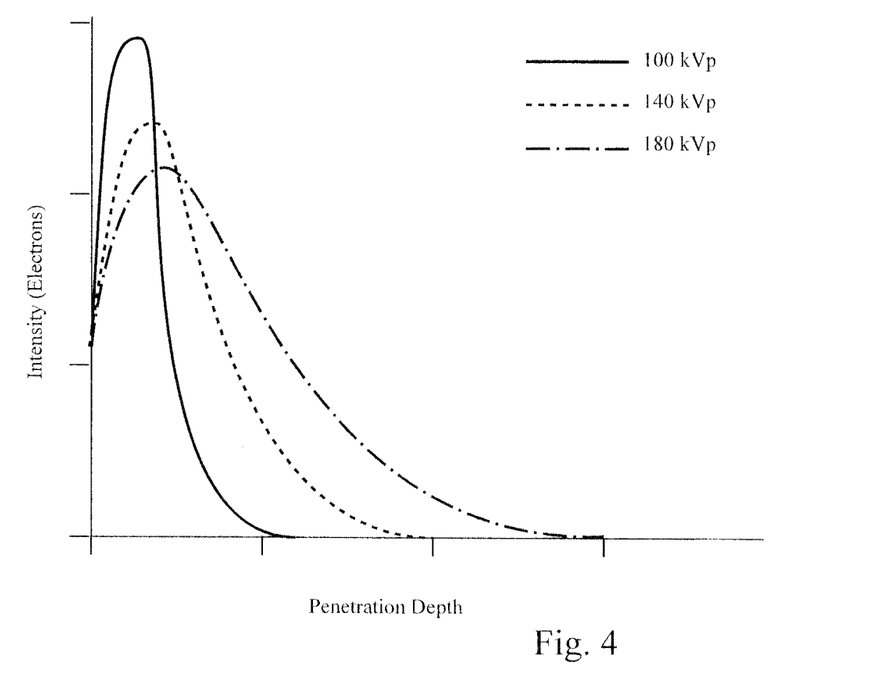
FIG. 4 is a diagram showing representative electron penetration depth profiles for electron beams of three different energies in a material.

FIG. 4 is a diagram showing representative electron penetration depth profiles for electron beams of three different energies in a material. The x-axis can represent penetration depth, for example in tens of microns. The y-axis can represent intensity, for example in microamps or arbitrary units. It can be seen that the lowest energy, e.g. 100 kVp, profile has the highest peak and fastest fall-off. Lower energy electrons can have a higher probability of attenuation, resulting in a large number of electrons being absorbed within a short depth, e.g. the high peak, and few electrons penetrating the material very deeply, e.g. the fast fall-off. The penetration depth and the width of the depth profile can increase with incident electron energy. Electron penetration depth profiles can also be dependent on the target material. The penetration depths at which peaks and fall-offs occur may be different for different target materials.

Figure 5:
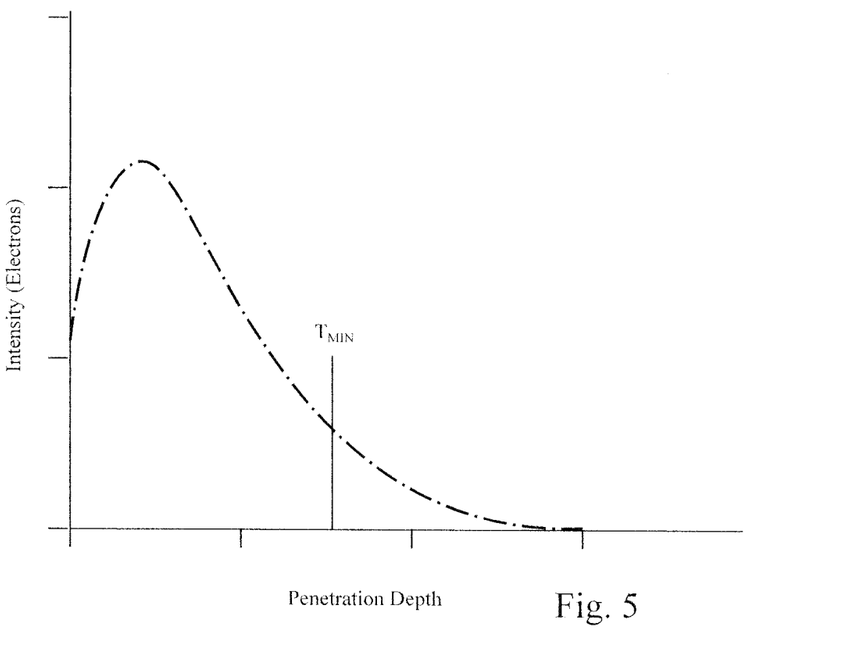
FIG. 5 is a diagram showing an electron penetration depth profile on one embodiment of the present invention.

A penetration depth profile may be integrated to determine the percentage of electrons from the incident electron beam which are likely to be absorbed by the material within a given depth. For example, integrating a depth profile from zero microns to a penetration depth where the profile has dropped to zero, e.g. infinite, can yield 100% of the electrons in the incident beam. This quantity can be used to normalize other integrations, such as to obtain a fraction or percentage of total electrons which are absorbed within a given depth. FIG. 5 is a diagram showing an electron penetration depth profile on one embodiment of the present invention. Integrating the profile from zero microns to a shorter depth, e.g. $T_{MIN}$ on the tail of the profile shown in FIG. 5, can then yield the percentage of incident electrons which may be absorbed before or at the shorter depth.

In one embodiment of the present invention, an anode that can serve as both a reflection and transmission target can have a target material layer thickness equal to an electron penetration depth at which at least 70% of the incident electrons are likely to be absorbed, given a predetermined electron energy. For example, the diagram of FIG. 5 may represent a penetration depth profile for electrons of a predetermined energy in the target material utilized in an embodiment of the present invention. Integration of the depth profile from zero microns to $T_{MIN}$ may yield 70% of incident electrons. The layer of target material may be $T_{MIN}$ microns or greater.

Alternatively, a layer of target material in the transmission-reflection anode may be equal to a depth at which between 50% and 100% of incident electrons are likely to have been absorbed. Determination of this thickness, e.g. depth, for a given target material and electron beam energy can be accomplished as previously described. The thickness may be a depth at which 50% to 60%, 60% to 70%, 70% to 80%, 80% to 90% or 90% to 100%, inclusive, of incident electrons are likely to be absorbed. For example, the layer of target material may have a thickness which is likely to absorb 91%, 92%, 93%, 94%, 95%, 96%, 97%, 98%, or 99% of incident electrons, or any other non-integer percentage between the enumerated values.

The following table presents ranges of layer thicknesses which may be utilized in some embodiments of the present invention for a selection of target materials and electron beam energies. Embodiments of the present invention are not limited to these ranges, materials, and energies.

| Material | Energy | Thickness |
| --- | --- | --- |
| Tungsten | 30 kVp | 2 µm-4 µm |
| | 60 kVp | 3 µm-6 µm |
| | 120 kVp | 7 µm-14 µm |

-continued

| Material | Energy | Thickness |
|---|---|---|
| Molybdenum | 30 kVp | 2 μm-4 μm |
|  | 60 kVp | 4 μm-8 μm |
|  | 120 kVp | 14 μm-28 μm |
| Niobium | 30 kVp | 2 μm-4 μm |
|  | 60 kVp | 4 μm-8 μm |
|  | 120 kVp | 14 μm-28 μm |
| Rhenium | 30 kVp | 2 μm-4 μm |
|  | 60 kVp | 3 μm-6 μm |
|  | 120 kVp | 7 μm-14 μm |
| Gold | 30 kVp | 2 μm-4 μm |
|  | 60 kVp | 3 μm-6 μm |
|  | 120 kVp | 7 μm-14 μm |

Increasing layer thickness of the target material can decrease the ratio of transmission X-rays to reflection X-rays produced by the anode upon excitation by an electron beam. In some embodiments of the present invention, the ratio of transmission X-rays to reflection X-rays can be 50:50. Alternatively, this ratio may be any ratio between 20:80 and 80:20, inclusive. This ratio may further be between 25:75 and 75:25, 30:70 and 70:30, 35:65 and 65:35, 40:60 and 60:40, or 45:55 and 55:45, inclusive.

In some embodiments of the present invention, the ratio of transmission X-rays to reflection X-rays can be tailored in a manner to produce a uniform X-ray flux at a predetermined boundary. For example, in an embodiment comprising a target material deposited on an inner surface of a spherical shell of substrate material described below, a uniform flux at the boundaries of the spherical shell may be desirable. The ratio of transmission X-rays to reflection X-rays may be less than 50:50 to account for a $1/r^2$ decrease in flux by reflected X-rays, attenuation of reflection X-rays by a cathode, or other factors. A ratio producing a uniform X-ray flux at a predetermined boundary can be determined by Monte Carlo simulation.

In a further embodiment, an approximation for a transmission-reflection anode thickness may be obtained by dividing the energy of an incident electron beam, e.g. in kVp, by ten, and assuming that this number, in microns, may be a thickness at which most electrons in the beam will have been attenuated. For example, an anode in a source utilizing a 180 kVp beam of electrons may have a thickness of approximately 18 μm to serve as both a reflection and transmission target. It may also have a thickness in the range of 13 μm to 23 μm, 15 μm to 21 μm, or 17 μm to 19 μm, inclusive. This approximation may be valid for anode materials including tungsten, gold, molybdenum, and others, though variability between materials may exist.

In embodiments of the present invention, a transmission-reflection anode can be made from a target material including but not limited to tungsten, molybdenum, or gold. In some embodiments wherein a thin-layer target is used the target material can be deposited on a substrate that has low attenuation properties for the resulting X-rays. The substrate can also have sufficient structural strength to withstand vacuum, as vacuum is maintained within X-ray sources to facilitate electron transit, and the force of incident electrons during X-ray production. Substrate materials may include but are not limited to beryllium, beryllium oxide, aluminum, aluminum oxide, aluminum nitride, boron carbide, boron nitride, and similar materials, such as structural ceramics. The substrate may be between 0.1 mm and 5 mm thick. For example, the substrate may have any thickness in the ranges of 0.5 mm to 4 mm, 0.5 mm to 3 mm, or 0.5 mm to 2 mm, inclusive.

In one embodiment of the present invention, the anode may comprise a spherical shell of a substrate material with a target material deposited over an inner section part, e.g. an inner hemisphere, of the substrate shell. The shell can also serve as or be part of a vacuum chamber through which electrons can travel to the target material. Electrons may be provided by a cathode located inside or outside the substrate shell.

The radius of a substrate shell in embodiment of the present invention may be between 2 mm and 1 cm. The radius of a substrate shell may be selected which is small enough to be inserted through an orifice to a surgical cavity, but which is large enough to be efficiently manufactured. This radius may further be in the range of 2 mm to 7 mm, 2 mm to 5 mm, or 5 mm to 7 mm, inclusive, or any integer or non-integer number of millimeters within the enumerated ranges. The radius of a semi- or hemispherical layer of target material may also be within the enumerated ranges, as the layer may be deposited on the substrate.

This embodiment may further comprise two concentric containment structures, e.g. an inner and outer containment structure. The inner containment structure may be a fixed-size containment structure such as a spherical metal shell or non-compliant balloon. A coolant fluid such as water or solution may be circulated between the substrate shell and a fixed-size inner containment shell. The radius of a fixed-size inner containment shell may be tailored to the radius of a substrate shell. For example, the radius of a fixed-size inner containment shell may be between 1 mm and 7 mm larger than the radius of a substrate shell it contains. It may further be between 2 mm and 6 mm, 2.5 mm and 5 mm, or 3 mm and 4 mm, inclusive, or any other integer or non-integer number of millimeters within the enumerated ranges. For example, a 3 mm gap may exist between a substrate shell and a fixed-size containment structure within which a coolant fluid can flow.

In this embodiment, the outer containment structure may be a compliant or non-compliant balloon. While the X-ray source and inner containment structure may have a fixed size, the outer containment structure may be expandable to a variety of cavity sizes, or may be selected to match a predetermined cavity size. Thus, an X-ray source and inner containment structure of fixed size may be utilized for brachytherapy across a range of cavity sizes, where the outer containment structure can be configured to accommodate the different cavity sizes. The outer containment structure may be filled with an X-ray inert gas such that the hardness of X-rays may be preserved between the inner containment structure and the outer containment structure; the hardness of X-ray beams reaching the treatment margin may be determined by the X-ray source and containment structures, e.g. independent of the size of the cavity.

If a radiation pattern of uniform hardness is created at the boundaries of an inner fixed-size containment, in this and similar embodiments, the radiation pattern created at the treatment margin may also have uniform hardness. Uniform hardness can refer to variation in beam hardness, e.g. in the mean of the X-ray energy distribution, having less than 20% variation at different angles, e.g. locations on a surface or boundary. In embodiments of the present invention, this uniformity may exist over approximately 80% or more of the 4π sr solid angle around an X-ray source. The uniformity may exist over less than 100% of the solid angle since the housing, vacuum tube, catheter, or other structures extending from the X-ray source and containment structure outside the cavity may obstruct or affect up to 20% of the solid angle of the radiation pattern. However, as these structures may be inserted through a hole in the treatment margin, their effect on the radiation pattern in that direction (e.g. toward a hole in the treatment margin) may not be a significant detriment to the treatment.

The radius of a spherical outer containment structure in this embodiment of the present invention may be between 5 mm and 3 cm. A spherical outer containment shell can have a predetermined radius, e.g. be a non-compliant balloon selected for a cavity of a known size, or achieve a range of radii, e.g. be a semi-compliant balloon inflated until it fills and slightly stretches a cavity. The radius or achievable radii of a spherical outer containment structure may further be in the range of 5 mm and 2.5 cm, 5 mm and 2 cm, 7 mm and 2 cm, 1 cm and 2 cm, inclusive, or any other integer or non-integer number of millimeters or centimeters within the enumerated ranges.

In a similar embodiment of the present invention, the anode may be shaped like a half ellipsoid or similar. For example, in one embodiment of the present invention, anode 31 in FIG. 3 can be a reflection and transmission target. Anode 31 may be a layer of target material deposited on ellipsoidal substrate 34. In this embodiment, both the upper hemisphere and lower hemisphere of containment structure 21 may be irradiated by anode 31. Cathode 32 may be may be small, e.g. point-source of electrons, in order to minimize the probability of X-rays reflected from anode 31 interacting with cathode 32. The shape of anode 31 may be tailored such that transmitted and reflected X-rays result in a uniform or nearly uniform radiation pattern around containment structure 21.

For example, in an embodiment of the present invention substrate 34 may have the same ellipsoidal shape as containment structure 21, with smaller dimensions. Transmission and reflection X-rays can produce a uniform radiation pattern at the boundaries of substrate 34. The distance between substrate 34 and containment structure 21 may constant, the structure having the same shape, such that the intensity and hardness of the radiation pattern may be preserved between the boundaries of substrate 34 and containment structure 21. In this manner, an ellipsoidal anode may create a uniform radiation pattern in an ellipsoidal containment structure or cavity.

Anode 31 may be oriented perpendicularly to major axis 33 of an ellipsoidal containment structure as shown in FIG. 3, but may also be oriented in parallel with axis 33 or in any other manner; surfaces other than an upper hemisphere of substrate 34 may be coated with a target material. For example, as shown in FIG. 3, the curved surface comprising anode 31 is centered at a point 90° relative to axis 33 in the forward-to-back direction. However, anode 31 may also be oriented such that its geometric or geographical center is located at 0°, 30°, 45°, 60°, or 90° relative to axis 33 in this, or other, directions. Anode 31 may also be centered at a point located between 0° and 20°, 20° and 40°, 40° and 60°, 60° and 80°, 80° and 100°, 100° and 120°, 120° and 140°, 140° and 160°, or 160° and 180°, inclusive, or any other integer or non-integer number of degrees within the enumerated ranges.

In this embodiment, the shape of anode 31 can be a half or partial ellipsoid, including a half or partial sphere as previously described. The shape of anode 31 may be tailored to create uniform radiation pattern in the treatment margin with transmitted and reflected X-rays. In an embodiment of the present invention utilizing a spherical containment structure, anode 31 may be spherical or ellipsoidal, positioned in the center of the containment structure, and produce a spherically uniform radiation pattern. In an embodiment of the present invention utilizing an ellipsoidal containment structure, anode 31 may also be spherical or ellipsoidal, positioned in the center of the containment structure, and produce a spherically uniform radiation pattern. Alternatively, anode 31 may be configured produce a uniform radiation pattern in the treatment margin in conjunction with the $1/r^2$ fall-off in X-ray intensity within the ellipsoidal structure, or may be positioned off-center within the containment structure.

Linear ray-tracing approximations, detailed Monte Carlo simulations, or any other method may be utilized to determine the radiation pattern which may be emitted by a transmission-reflection anode in this embodiment of the present invention. One or more containment structures may contain the anode. The containment structure or structures can uniformly attenuate incident X-rays or may have thickness variations which selectively attenuate X-rays. The structure or structures may also be filled with an X-ray attenuating or X-ray inert medium.

Alternatively, the shape of anode 31 may be tailored to create a predetermined, non-symmetric radiation pattern. In other embodiments of the present invention, the anode may serve primarily as a transmission target or primarily as a reflection target. A primarily-reflection target may have a thickness in the range of 1 µm to 500 µm. However, the anode thickness at which most X-rays travelling in a forward direction will be attenuated prior to emission from the anode, causing the anode to be a primarily-reflection target, may depend on the energy of incident electrons. Energetic electrons may permeate a greater depth of material than less energetic electrons. For example, in a source utilizing a 180 kVp electron beam a primarily-reflection target may have a thickness of 20 µm to 40 µm, 25 µm to 35 µm, or 27 µm to 30 µm, inclusive. In a source utilizing a 100 kVp electron beam, a primarily-reflection target may have a thickness of 7 µm to 30 µm, 8 µm to 20 µm, or 10 µm to 15 µm, inclusive.

Figure 6:
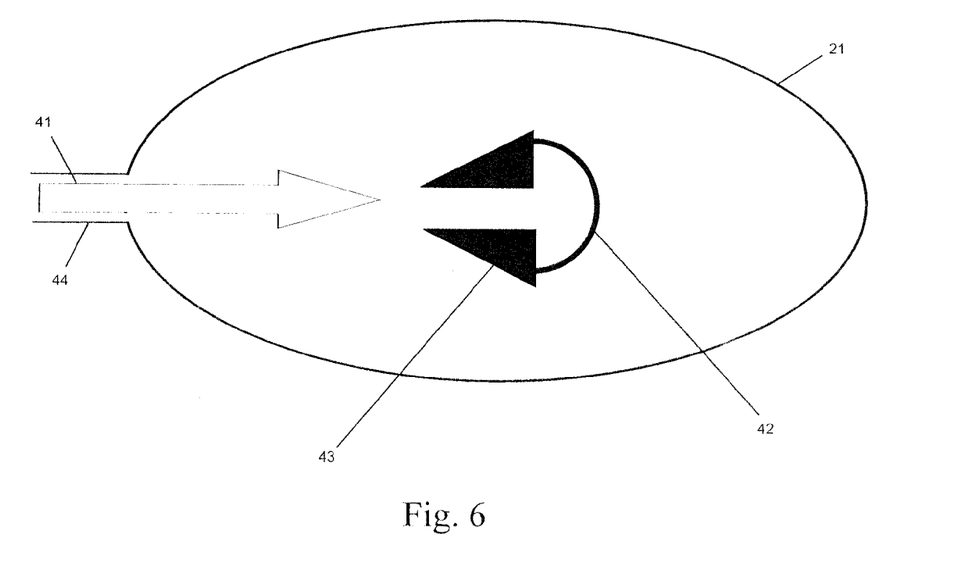
FIG. 6 is a diagram showing an embodiment of the present invention wherein the anode is divided in separate sections.

FIG. 6 is a diagram showing an embodiment of the present invention wherein the anode is divided in separate sections. In this embodiment of the present invention, one section may serve as a transmission target while another section serves as a reflection target. For example central X-rays of the beam 41 can hit transmission target 42 while relatively outer X-rays of beam 41 can hit reflection target 43. Beam 41 may be generated by an internal or external cathode. If generated by an external cathode, beam 41 can enter containment structure 21 through evacuated tube 44 as shown. Evacuated tube 44 may be part of an overall vacuum chamber containing the cathode and anode.

Similar embodiments of the present invention may utilize alternative geometries or configurations to create a multi-part anode which can serve as both a reflection and transmission target. Multi-part anodes may be tailored to generate uniform radiation patterns in the treatment margin. Alternatively, multi-part anodes may be tailored to generate directional radiation patterns.

In another embodiment of the present invention an electron beam can be steered to particular parts of the anode and selectively create a radiation pattern from parts of the anode. The electron beam can be steered by a method or methods including but not limited to magnetic or electric lensing or deflection. The electron beam can be generated by a cathode located within or outside the surgical cavity or containment structure.

FIG. 7 is a diagram showing an embodiment of the present invention, wherein the anode is a spherical transmission target with only a small opening for insertion of the cathode. The small opening in spherical anode 51 may be circular with diameter ranging from 1 mm to 5 mm, inclusive, and may be tailored to the size of anode 51 and cathode 52.

In one embodiment of the present invention, the electron emitter is a heated disk with sharp edges to facilitate field emission of electrons. The rate or amount of electron emission from a conductive surface can be correlated with the strength of the electric field at the surface. Sharp edges or points, e.g. high aspect ratios, on an electrically conductive surface can locally enhance the electric field at these points and thereby increase the probability of field emission from the surface at a given voltage difference between anode and cathode.

In another embodiment the cathode is made from carbon nanotubes. Single carbon nanotubes or a bunch or bunches of carbon nanotubes may be grown on a flat, curved, or any other surface. The nanotubes or bunches of nanotubes may serve as very sharp points for field emission; carbon nanotubes may have a length-to-diameter up to 132,000,000:1. In another embodiment of the present invention, the cathode is a sphere of emitter wires or carbon nanotubes, e.g. having the appearance of a "fuzz ball," that may or may not be heated. For example, carbon nanotubes may be grown individually or in bunches from the surface of a sphere. This type of spherical, field-emission cathode may be utilized in an embodiment of the present invention with a spherical anode, such as in FIG. 7, or with other anode geometries. For example, a spherical, field-emission cathode comprising carbon nanotubes may be utilized in conjunction with an ellipsoidal transmission-reflection anode producing a uniform radiation pattern.

In another embodiment of the invention the electron emitter can be a thermionic emitter such as a hot filament or a dispenser-type cathode.

In one embodiment of the present invention, any combination of the previously described containment structures and radiation sources may be utilized for irradiation of a surgical cavity following a mastectomy or lumpectomy. The radiation pattern may be uniform or may be tailored to under-dose ribs or other bones and skin surfaces of a patient, for example by rotating the source or shaping the anode or containment structures. One or more containment structures, e.g. a balloon with or without an inner containment structure, may be placed within a cavity during the procedure. An opening to the cavity can be left to accommodate insertion of a radiation source for radiation treatments during the hours or days following the mastectomy or lumpectomy. The opening can be sutured shut upon completion of radiation treatments and removal of the containment structure or structures.

Figure 8:
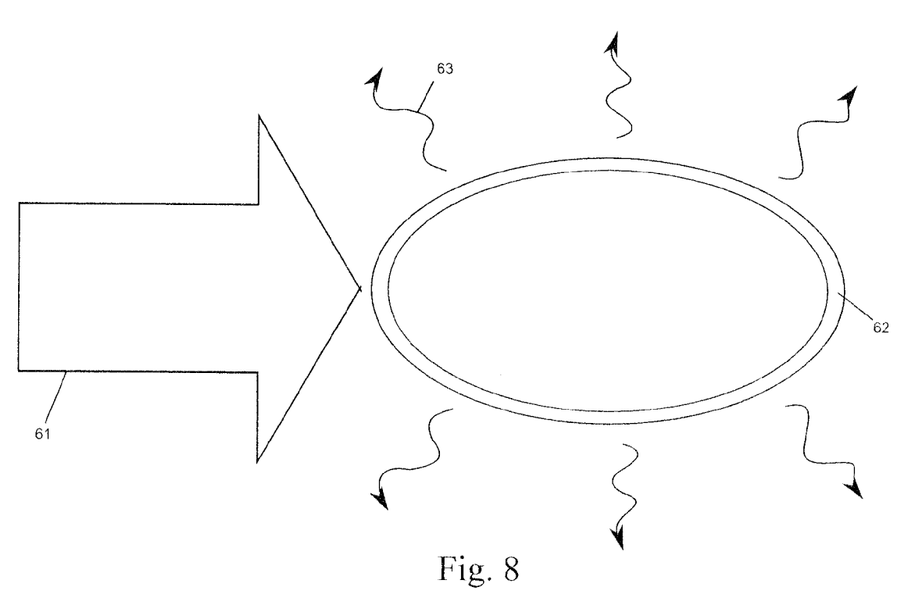
FIG. 8 is a diagram showing an embodiment of the present invention comprising a balloon or other structure that is coated with a fluorescing agent.

FIG. 8 is a diagram showing an embodiment of the present invention comprising a balloon or other structure that is coated with a fluorescing agent. Fluorescing agents which may be utilized in this embodiment include but are not limited to iodine, zirconium, molybdenum, niobium, gold, or similar. This embodiment can utilize an external X-ray source, which may be moved around the patient during treatment. Irradiation of the fluorescing agent by an external source can generate fluorescence radiation, which can then irradiate the treatment margin; X-ray beam 61 may excite a fluorescing agent in coating 62, the resultant X-ray fluorescence 63 then irradiating a surrounding treatment margin.

In another embodiment, the fluorescing agent can be incorporated in a catheter. For example a plug or a balloon can be delivered directly to lesions in the vasculature or to a nerve for targeted ablation. The plug can be made from metal such as gold and can have geometries similar of those used in stents. For example, a plug or balloon can be a very narrow cylinder, e.g. a cylinder with a diameter between 1 mm and 5 mm, or any other shape allowing for delivery to a targeted location inside a blood vessel via catheter or other means.

Plugs or balloons can have non-uniform coatings or shapes to allow for a non-uniform radiation pattern particularly treating the target volume and sparing healthy tissue.

In these embodiments, an external X-ray source can have a peak voltage between 20 kVp and 250 kVp, inclusive. Alternatively, in some embodiments of the present invention the external X-ray source can have a peak voltage up to 500 kVp. The X-ray source may also have a peak voltage in the range of 60 kVp to 100 kVp, 60 kVp to 150 kVp, or 80 kVp to 250 kVp, inclusive.

In an embodiment of the present invention, the peak voltage of the external X-ray source can be related to the type of fluorescing agent utilized. For example, the peak voltage can equal or be just above the binding energy of the atomic k-shell of the fluorescing agent, e.g. the k-edge of the agent. A photoelectric interaction, the ejection of an electron from the k-shell of an atom by a photon, can result in X-ray fluorescence as an electron in a higher energy atomic shell may release energy in the form of an X-ray photon in order to fill the hole created in the k-shell. In this embodiment, the probability of photoelectric interaction between X-ray photons from the external source and electrons in the fluorescent agent may be maximized. Thus, this embodiment can also maximize the amount of targeted fluorescence delivered to surrounding tissue. Furthermore, electrons scattered via photoelectric interactions can also travel into surrounding tissue and have some treatment benefit.

In an additional embodiment of the present invention, a fluorescing agent can be chosen to optimize the delivery of targeted fluorescence. In this embodiment, the k-edge of the fluorescing agent can be sufficiently high such that X-ray photons from an external source that are tailored to the k-edge can have a low probability of absorption in tissue between the source and balloon or plug. This k-edge may be greater than 60 KeV, 70 KeV, 80 KeV, or higher. Gold, for example, has a k-edge of approximately 81 KeV.

The external X-ray source can be a conventional X-ray source, e.g. a point-source X-ray tube, or may be a scanning-beam digital X-ray source or multi-cathode X-ray source such as a plurality of carbon nanotubes. The energy spectrum of the X-ray source and the attenuation properties of this embodiment can be adjusted to achieve a desired depth-dose profile. Additionally, the irradiation path of the external X-ray source can be designed to produce an intentional non-uniform radiation pattern.

In one embodiment of the present invention, a plug or balloon coated with or consisting of a fluorescent agent can be inserted into a vein or artery from which a blockage has been cleared via angioplasty or another method. The plug or balloon can be irradiated by an external X-ray source, and resulting X-ray fluorescence from the plug or balloon can treat the walls of the vein or artery that has recently been cleared. This treatment can decrease the probability of subsequent tissue growth in the area re-blocking the vessel. This embodiment may be particularly useful for the treatment of coronary artery disease, peripheral vascular disease, or similar conditions. This embodiment may be superior to conventional brachytherapy as it does not require the introduction of radioactive materials into the operating room or catheter lab.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A system for electronic brachytherapy comprising:
a vacuum chamber for transit of electrons;
a cathode within said vacuum chamber for emission of said electrons; and
an anode within said vacuum chamber, wherein said anode has a first section configured as an x-ray transmission target and a second section configured as an x-ray reflection target and wherein said first section of said anode and said second section of said anode are configured to simultaneously receive said electrons and to simultaneously generate transmission x-rays and reflection x-rays.

2. The system of claim 1 wherein said anode comprises a metal with an atomic number greater than 40.

3. The system of claim 1 wherein said anode is configured to absorb at least 50% of said electrons striking said anode.

4. The system of claim 1 wherein said thickness of a layer of said anode is between 1 μm and 150 μm.

5. The system of claim 1 wherein said vacuum chamber comprises a shell of substrate material.

6. The system of claim 5 wherein said shell is spherical.

7. The system of claim 6 wherein said layer is deposited on an inner surface of said shell.

8. The system of claim 5 wherein said shell is ellipsoidal.

9. The system of claim 5 wherein wall of said shell is between 0.1 mm and 5 mm thick. thick.

10. The system of claim 1 further comprising:
a layer of substrate material between 0.1 mm and 5 mm thick within said vacuum chamber.

11. The system of claim 10 wherein a layer of target material is deposited on said layer of substrate material.

12. A system for electronic brachytherapy comprising:
a vacuum chamber;
a cathode within said vacuum chamber;
an anode within said vacuum chamber, wherein said anode has a first section configured as an x-ray transmission target and a second section configured as an x-ray reflection target and wherein said first section of said anode and said second section of said anode are configured to simultaneously receive said electrons and to simultaneously generate transmission x-rays and reflection x-rays;
a fixed-size containment structure around said vacuum chamber;
an X-ray attenuating coolant fluid within said fixed-size containment structure;
an inflatable balloon around said fixed-size containment structure; and
an X-ray inert gas within said inflatable balloon.

13. The system of claim 12 wherein said X-ray attenuating coolant fluid is an ionic solution.

14. The system of claim 13 wherein said ionic solution comprises ions of an element with an atomic number greater than 11.

15. The system of claim 14 wherein said ionic solution comprises iodine.

16. The system of claim 12 wherein a gap between walls of said vacuum chamber and said fixed-size containment structure for said coolant fluid is between 1 mm and 7 mm.

17. The system of claim 12 wherein said X-ray inert gas is air.

18. The system of claim 12 wherein said X-ray inert gas is nitrogen.

19. The system of claim 12 wherein said X-ray inert gas is helium.

20. The system of claim 12 wherein said vacuum chamber, said X-ray attenuating coolant fluid, and said fixed size containment are configured to produce an X-ray radiation pattern of uniform hardness around said fixed-size containment structure.

* * * * *